United States Patent [19]

Bostick et al.

[11] 4,357,420

[45] Nov. 2, 1982

[54] BIOLUMINESCENCE METHODS FOR ENZYMATIC DETERMINATIONS

[75] Inventors: William D. Bostick, Oak Ridge; Mark S. Denton, Clinton; Stanley R. Dinsmore, Norris, all of Tenn.

[73] Assignee: The United States of America as represented by the United States Department of Energy, Washington, D.C.

[21] Appl. No.: 258,350

[22] Filed: Apr. 28, 1981

[51] Int. Cl.³ .................. C12Q 1/66; C12Q 1/50; C12Q 1/32; C12M 1/34

[52] U.S. Cl. .................. 435/8; 435/17; 435/26; 435/291; 435/808; 422/81

[58] Field of Search .......... 435/8, 17, 26, 4, 803, 435/808, 291, 288, 289; 422/81; 424/7

[56] References Cited

U.S. PATENT DOCUMENTS

| | | | |
|---|---|---|---|
| 4,263,406 | 4/1981 | Bostick et al. | 435/291 |
| 4,278,760 | 7/1981 | Wulff et al. | 435/8 |
| 4,278,761 | 7/1981 | Hastings et al. | 435/8 |
| 4,286,057 | 8/1981 | Wulff et al. | 435/8 |

OTHER PUBLICATIONS

Birks, T. W., et al., "Chemiluminescent Aerosol Spray Detector Liquid Chromatography", Anal. Chem., vol. 52, pp. 879-901, (1980).
Kobayashi, S., et al., "Determination of Fluorescent Compounds by High Performance Liquid Chromatography with Chemiluminescence Detection", Anal. Chem., vol. 52, pp. 424-427, (1980).
Veazey, R. L., et al., "Chemiluminescence High-Performance Liquid Chromatography Detector Applied to Ascorbic Acid Determinations", Jour. Chromatography, vol. 200, pp. 153-162, (1980).

*Primary Examiner*—Benoit Castel
*Attorney, Agent, or Firm*—Clay C. Carter; Stephen D. Hamel; Richard G. Besha

[57] ABSTRACT

An enzymatic method for continuous, on-line and rapid detection of diagnostically useful biomarkers, which are symptomatic of disease or trauma-related tissue damage, is disclosed. The method is characterized by operability on authentic samples of complex biological fluids which contain the biomarkers.

6 Claims, 3 Drawing Figures

BIOLUMINESCENCE METHODS FOR ENZYMATIC DETERMINATIONS

The invention is a result of a contract with the United States Department of Energy.

BACKGROUND OF THE INVENTION

This invention relates to quantitative analysis of chromatographic effluents containing biomarkers symptomatic of disease states and tissue injury in humans.

Biomarkers of interest are proteins or isoenzymes (enzymes which catalyze the same reaction) found in complex biological matrices such as tissue, serum, urine, and other body fluids. These biomarkers provide a non-evasive means of clinical diagnosis. Accurate biomarker profiling of integrated clinical samples, however, has been difficult because of monitor response to interferring species causing erroneous analysis. Interferents in human biological samples can be endogeneous constituents, drugs, proteins, or metabolites, which respond at about the same wavelength as the biomarker of interest. Conventional compensatory methods have done little to improve accuracy and sensitivity. Thus, direct analysis of patient-derived samples has been limited.

One successful approach for proper analyses of biological samples is described in coassigned application Ser. No. 062,375, filed July 31, 1979 entitled "Method for Continuously Referenced Analysis of Reactive Components in Solution," now U.S. Pat. No. 4,263,406. A referenced, self-blanking system is disclosed therein for biomarker profiling of creatine kinase (CK,EC 2.7.3.2) and lactate dehydrogenase (LD,EC 1.1.1.27). Compensation for interferents is provided by a dual-channel flow system derived from a common source. Subtraction of a reference stream from a sample stream therein generates an indicator-species response correlatable to the profiled biomarker.

While self-referencing analysis produces reliable diagnostic assays, nonreferenced systems remain unreliable and of limited utility. Recently, the phenomena of ozone or peroxide-induced chemical luminescence have been described as a highly selective and extremely sensitive technique for analytical purposes.

Birks, T. W., et al., in "Chemical Luminescent Aerosol Spray Detector for Liquid Chromatography," Anal. Chem., 52, pp. 897-901 (1980) has quantitated highly fluorescent compounds by nebulizing a simple chromatographic effluent with a high velocity stream of $O_2$ and $O_3$ gases. Detection of the resultant ozone induced chemiluminescence has provided an accurate mass detection in the microgram to picogram range. The hazards of working with flammable concentrations of $O_2/O_3$ gases and organic compounds are also discussed along with potential toxic wastes.

Another recent article has applied chemiluminescence to determine artificial samples of four dansylated amino acids. Kobayashi, S., et al., in "Determination of Fluorescent Compounds by High Performance Liquid Chromatography with Chemiluminescence Detection," Anal. Chem., 52, pp. 424-427 (1980) used laboratory reagents of hydrogen peroxide and oxalic esters to detect femtomole concentrations of the analyte. Authentic biological specimens were not therein analyzed.

Finally, Veazey, R. L., et al., in "Chemiluminescence High Performance Liquid Chromatographic Detector Applied to Ascorbic Acid Determinations," J. Chromatogr., 200, pp. 153-162 (1980) applied chemiluminescence detection to ascorbic acid and other organic reductants in basic media. The reactions involved are performed under optimal conditions and apply to any reducing agent. Only ascorbic acid was quantitated at truly useful concentrations. Reactant instability and variant flow rates necessitated frequent recalibration or addition of fresh reagents.

STATEMENT OF THE OBJECTS

It is an object of this invention to provide a method useful for analyzing and quantifying biomarkers of authentic biological specimens, said method and monitor characterized by bioluminescence detection of high specificity for the biomarker of interest.

It is a final object of this invention to provide a method useful for proper analysis of tissue-specific biomarkers in a nonreferenced and noncompensated analytical system.

SUMMARY OF THE INVENTION

The foregoing and other objects are satisfied by the monitor used in the present invention comprising, in combination: conduit means for conducting a sample solution, such as an authentic, human biological sample, from a source of said solution; stream diversion means disposed within said conduit for separating said sample solution into first and second streams, wherein said first stream is only a minor portion of the original solution; means disposed in fluid communication with said first stream for introducing and independently regulating the flow thereto of one or more reactants; means disposed within said first stream for incubating said reactants and sample portion for sufficient time and temperature to produce a bioluminescent response; and means disposed within said first stream for monitoring said response, said response intensity being correlatable to a biomarker concentration contained within said sample solution.

Biomarkers of interest can be catalytically active, causing a reaction to occur between introduced reactants, or the biomarkers can be chemically reactive with the reactants to generate an ultimate bioluminescent response. A potential source for the sample solution could be an ion exchange column or other apparatus performing chromatographic separations. Generally, the first stream will be only a small volumetric percentage (5 vol.%) of the original sample solution. This permits lower reagent consumption and better flow control in our monitor, thus reducing cost and increasing replicate application reliability. Further, reaction time and bioluminescent intensity are also enhanced by reduced flow providing greater sensitivity. Typically, soluable or immobilized indicator enzymes can be used in our monitor within the reaction zone. The monitoring means can be a simple, flow-through fluorometer without an excitation source or filters, which are responsive to bioluminescent intensity and correlates said intensity to biomarker concentration. An x-y recorder may be connected to the fluorometer for purposes of producing a permanent record of the assay.

DETAILED DESCRIPTION

Figure 1:
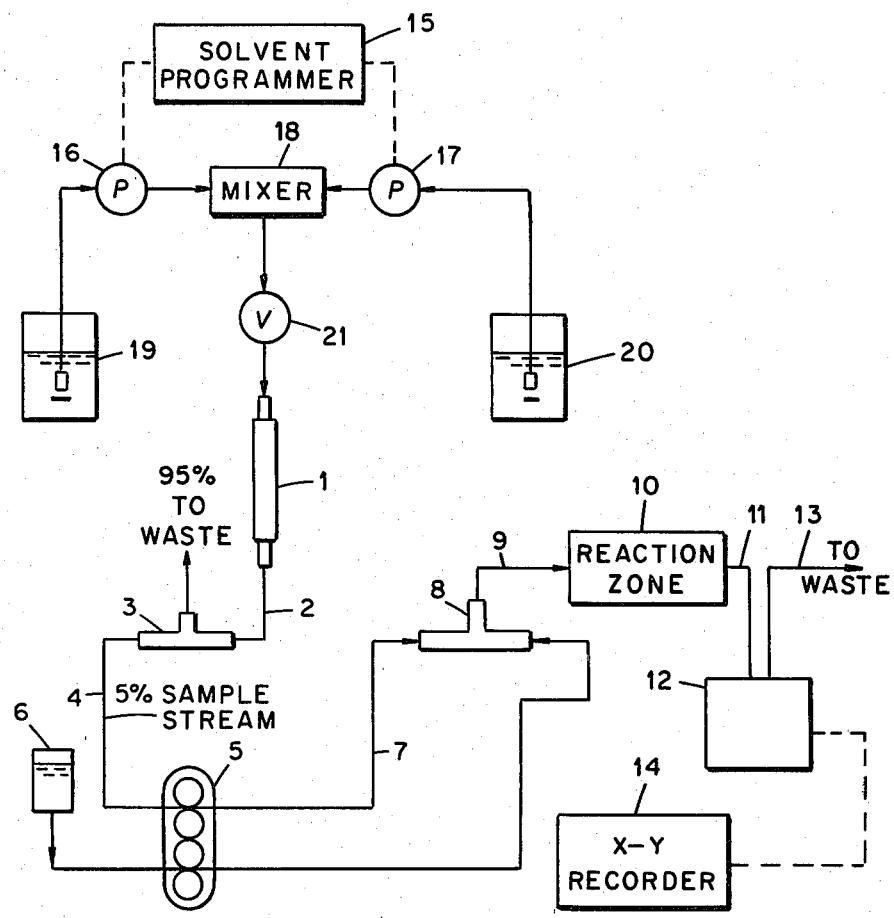
FIG. 1 is a schematic representation of an apparatus of this invention in combination with a chromatographic separation column.

The method of this invention is useful for quantitatively detecting and measuring the concentration of practically any biomarker in biological fluids which can be caused to participate in an enzymatic reaction or reactions to ultimately produce a bioluminescent response. It is particularly valuable in nonreferenced applications wherein accurate discrimination between pathology verifying biomarkers and other solution constituents is essential.

In accordance with this invention, a sample solution containing a biomarker species of interest is conducted from a source through a conduit wherein a predetermined amount, typically 5 vol.%, is diverted into an analytical monitor wherein said amount is contacted with an equal amount of one or more specific reactants for the biomarker of interest. The reactants may be added directly or generated in situ by addition of appropriate precursors. Generally, the biomarker will be catalytically reactive although some turnover at relatively slow rates may occur. Biomarkers and reactants are contacted in biologically effective amounts until a biolumenescent responding product luminophor is formed. This reaction should require no more than 20 minutes and a temperature range of about 25° to 40° C.

Oxidation of the reaction zone product will produce a visible light response which is monitorable at a wavelength of 550 to 650 nm. The necessary indicator enzymes or other reactants to produce this response are biomarker specific thus assuring selectivity and sensitivity. In situ generation of light within our invention eliminates major causes of error in other systems caused by aging, drift, or light source fluctuation, as well as light loss or scatter within the sample. This causes a higher signal to noise ratio thereby producing a chromatogram having a relatively stable base line. Therefore, our monitor can utilize greater signal amplification to produce greater sensitivity. We have found that enzyme-activated bioluminescent emissions give wavelength intensities producing good chromatograms with sharply defined, well-resolved peaks. Solution components which are not of interest do not give an indicating response thus obviating the need for species discrimination by referencing or other compensatory methods. Since only the biomarker of interest will metabolize a reactant substrate specifically prepared for its determination, improper analysis or ambiguous results are not a problem. A bioluminescent emission is confirmatory of the pathology associated with the biomarker being investigated and verifies damage or disease within tissue related to or a source of the biomarker. The emission intensity is also correlatable (directly proportional or otherwise) to biomarker concentration.

The nondiverted portion of sample solution (95 vol.%) can be wasted since sufficient analyte is provided to our monitor in the diverted stream for desired precision. Alternatively, it can be utilized as a source of feed to a series of monitors wherein several biomarker species can be simultaneously determined from a common biological sample. Different reactant substrates, specific for each biomarker being investigated, would be the only adaptation necessary for these monitors.

Such an embodiment is of particular interest where two or more isoenzymes may be symptomatic of the same pathology. For example, simultaneous CK and LD assays would provide virtually 100% diagnostic assurance of the incidence of myocardial infarction.

The following example is presented to illustrate preferred operable modes for carrying out the method of this invention. Process conditions are not necessarily optimized. These examples are for purposes of illustration and are not intended to be limiting, our invention being limited only by the claims. While only isoenzymes of CK and LD are demonstrated, the monitor and method of the present invention are theoretically applicable to any enzyme capable of generating a detectable bioluminescent responding species or product within a reasonable reaction time through use of enzyme coupled reactions. For instance, relatively few isoenzymes (about 4) are known to convert adenosine diphosphate (ADP) directly to bioluminescent responding species. Assays of those four isoenzymes would be analagous to Example I. There are approximately 150 other isoenzymes which can be coupled to the clinically significant NAD-NADP cofactor system as in Example II to indirectly produce bioluminescent responding species.

EXAMPLE I

Separation of Creatine Kinase Isoenzymes

A 30 cm stainless steel column for high-pressure ion exchange was acquired from Waters Associates, Milford, Mass. Referring to FIG. 1, this column 1 was slurry packed with SYNCHROPAK AX300 (10 μm) from Synchrom, Inc., Linden, Ind. Authentic serum samples from a hospital patient suspected to have experienced myocardial infarction were determined to contain 813 units per liter of total CK activity in a 50 microliter sample. One of these samples was loaded onto the column by introduction through injector valve 21 (by means of an alternate route not shown). Gradient elution was performed by a Waters Model 660 solvent programmer 15 into Waters Model 6000A pumps 16 and 17. The elution involved an initial five minute hold at the concentration of solvent A from reservoir 19 followed by 0–100% solvent B from reservoir 20. Solvent A was 0.03 M tris (hydroxy methyl) methylamine buffer (TRIS), adjusted to pH 7.4 by acetic acid while solvent B was 1.0 M lithium acetate, adjusted to pH 7.4 by lithium hydroxide. We found a lithium acetate gradient to have less of an inhibitory effect on luciferase indicator enzymes utilized in our monitor and its use is much preferred. Total column effluent (180 ml/hr) passed through line 2 into a stream diverter 3 which separated said flow by a 19:1 ratio. The diverted stream flow (1/20) of about 10 ml/hr is employed in the analytical monitor of the present invention. The remaining flow which is undiverted (19/20) is wasted for purposes of this example. The diverted stream flow is received into our monitor by peristaltic pump 5 which provides a like amount of flow (10 ml/hr) from reservoir 6 of a reactant substrate highly specific for CK. This reactant substrate has the following composition:

TABLE I

| Reactant Substrate For Creatine Kinase Isoenzyme Analysis | |
|---|---|
| Constituent | m mol/L |
| Creatine Phosphate | 10 |
| adenosine diphosphate (ADP, a cofactor) | 0.05 |
| imidazole acetate buffer (pH 7.4) | 50 |
| magnesium acetate (an activator) | 10 |

TABLE I-continued

| Reactant Substrate For Creatine Kinase Isoenzyme Analysis | |
|---|---|
| Constituent | m mol/L |
| *luciferin | * |
| *luciferase | * |
| mercaptoethanol (an enzyme activator) | 10 |
| tetrasodium ethylenediamine tetracetate (an enzyme-inhibition preventor) | 0.5 |

*In three separate tests we utilized different sources of the luciferin-luciferase reagent. These were LUMIT PM and LUMIT HS by Lumac, Inc., Westlake Village, California, which were added in one vial dilutions, respectively, to 10 ml of Table I's reagent solution. Pico-Zyme F by Packard Instrument Co., Downers Grove, Illinois was also used except one vial per 4 ml of reagent solution was added. Despite these high dilutions, we found sufficient detectability for the ATP reaction product at about 75% of the Lumac and 31% of the Packard proposed incubation concentrations. Optimum bioluminescent response is anticipated for the CK coupled to luciferin system at a pH of about 7.2 to 7.4.

Within our monitor, these equalized flows of about 20 ml/hr are supplied to a T-mixer 8 wherein contact and subsequent metabolization are initiated. This reaction continues during transport through said mixer, line 9, and reaction zone 10. For enzymatic determination of CK by luciferin, the reaction zone is a delay coil maintained at about 24° C. of sufficient length for about 2.5 minutes of residence to produce a detectable biolumenescent response. For other systems, variations in temperatures and residence times may be necessary dependent upon biomarker and reagent constituents.

The monitor of the present invention has a dynamic range of about $10^{-5}$ to $10^{-9}$ molar concentrations of ATP. Similar ranges for other bioluminescent responding species are expected. The CK-converted ADP does not require additional reactants or indicator enzymes as most other enzymatic methods. Firefly luciferase has only moderate storage stability and is subject to inhibition in high ionic strength media. Therefore, soluable enzymes which are wasted after the assays are utilized in reservoir 6. The overall reaction sequence for this assay can be written as follows:

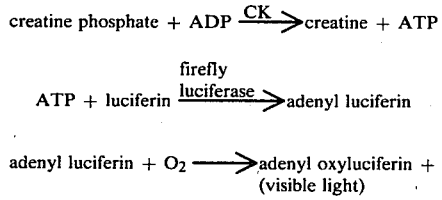

A bioluminescent emission that is observable for several minutes was monitored by flow through line 11 into an 18 μm sample cell of an Aminco Fluorometer 12 by American Instrument Co., Silver Spring, Md. Photomultiplier tubes within said fluorometer provide electrical signals proportional to bioluminescent response by integrating photon counting techniques. This response intensity can be correlated to concentration of the biomarker species of interest.

Figure 2:
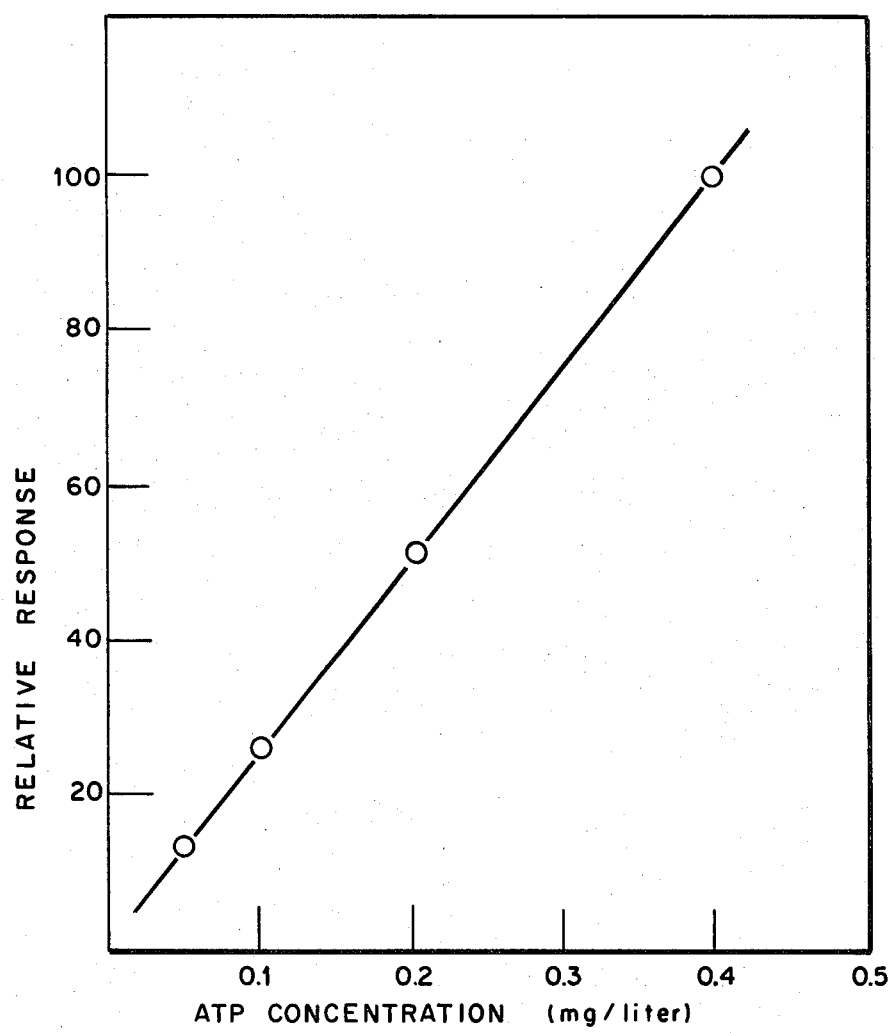
FIG. 2 is a graph of relative detector response as a function of ATP concentration showing a relationship between emission intensity and a bioluminescent responding species.

FIG. 2 is a graph for LUMIT HS reagent showing percent relative response of the fluorometer to ATP concentration in mg/L.

Figure 3:
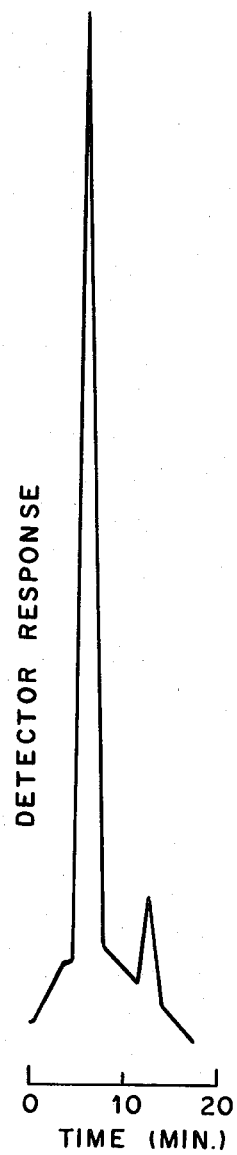
FIG. 3 is an absorbance curve of a continuously, nonreferenced analysis of creatine kinase in a serum sample according to this invention.

The output of the fluorometer can be reduced to a permanent record by means of a strip chart recorder 14. FIG. 3 is a typical chromatogram produced by the monitor of the present invention under the conditions described. Pico-Zyme F indicator enzyme was used to produce this chromatogram. Two distinct isoenzymes of CK can be clearly identified therein as the result of this assay. Proceeding from left to right in FIG. 3, CK-MM (predominant peak) eluted after about six minutes followed by CK-MB (minor peak) at about twelve minutes. A CK-BB peak was detected at about 17 minutes, but is not shown. Following detection, the assayed stream is wasted through line 13.

EXAMPLE II

Separation of Lactate Dehydrogenase

Detection and measurement of lactate dehydrogenase (LD, EC 1.1.1.27) can be accomplished in the apparatus of Example I wherein identical procedures are followed except as noted hereinafter. Since LD does not directly produce a bioluminescent emitting product or luminophor, product, the reactant substrate must be modified to couple the LD catalyzed reaction product to such an emission reaction. This can be accomplished through use of the enzymatic cofactors β-nicotinamide adenine dinucleotide (NAD) or β-nicotinamide adenine dinucleotide phosphate (NADP) within an oxidoreductase enzyme system utilizing flavin oxidoreductase. The following substrate could be utilized in such an assay:

TABLE II

| Reactant Substrate For Lactate Dehydrogenase Isoenzyme Analysis | |
|---|---|
| Constituent | Concentration m mol/L |
| Li-1-lactate | 50 |
| 2-amino-2-methyl-1,3-propanediol buffer (2-AMP-diol) (pH 8.5) | 10 |
| NADP | 3.5 |
| Dodecanal (lauryl aldehyde) | 10 |

The LD is detected by means of the following reaction sequence:

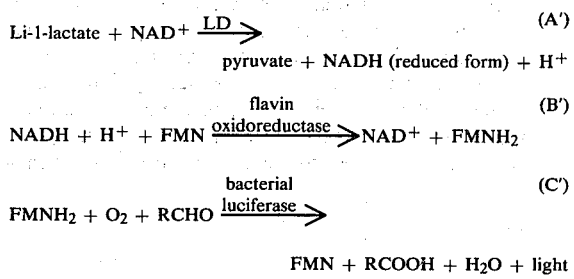

The reaction zone 10 of FIG. 1 must be modified to include a conduit segment or microreactor serially downstream of the delay coil or like reaction vessel. Reaction A' would take place in the delay coil in about 10 minutes at a temperature of about 37° C. while reactions B' and C' would take place in the microreactor in a matter of seconds. Co-immobilized enzymes and reactants of NADH, flavin mononucleotide (FMN), bacterial luciferase, and flavin oxidoreductase which are specific for NADH or NADPH coupled determinations are prepared by standard methods. See, for example, *Biotechnology and Bioengineering*, Vol. XVII, "High Performance Enzyme Reactors," pp. 1487–1491, John Wiley and Sons, Inc., (1978) and *Enzyme Engineering*, Vol. 2, Pye, E. K., et al., Eds., pp. 67–76, "Review of Recent Enzyme Immobilization Techniques," Plenum Press, New York. Techniques for co-immobilization of bacterial luciferase and flavin reductase are also disclosed by Tu, S-C., et al., Proceedings of the National Academy of Science, 77, pp. 249–252 (1980).

We have found removable microreactors containing immobilized enzymes in our monitor to have an additional advantage for their incorporation. Soluable enzyme substrates, such as used in Example I, are viable for about two days under refrigeration, after which, they must be discarded. The same substrates cannot be frozen because such temperatures inactivate their enzymes. This undesirably adds to the expense of the determination. However, isolation of indicator enzymes from reactant substrates by immobilization within microreactors remarkably improves refrigerated storageability of both substrate and enzymes. The microreactors being storable at about 5° C. for up to several months while the substrate can be frozen indefinitely at about −60° C.

It can thus be seen that a monitor and method for the nonreferenced, direct quantitation of biomarker activities at low-concentration levels have been provided by the present invention. Said monitor and method have direct application in clinical diagnostic settings to confirm suspected human pathologies. According to the present invention, biomarker assays can be performed in less than 20 minutes at substantial savings over presently available electrophoresis and other chromatographic methods. Definitive diagnosis by automated, on-line detection and quantitation of biomarkers is thereby rendered more practical and reliable.

What is claimed is:

1. A nonreferenced method for continuous, on-line and rapid detection of diagnostically useful biomarkers, which are symptomatic of disease or trauma-related tissue damage, said method characterized by operability on an authentic sample of complex biological fluids, containing a plurality of said biomarkers, comprising, in combination, the steps of:
   contacting a predetermined amount of the sample with an enzymatically effective amount of reactants to generate a specific bioluminescent emission correlatable to the concentration of a specific diagnostically useful biomarker isolated by liquid chromatography from said biomarker plurality; and
   monitoring the emission intensity to determine the specific biomarker concentration in a fluorometer characterized by the absence of an excitation source and filters.

2. The method of claim 1 wherein the biomarker of interest is creatine kinase.

3. The method of claim 1 wherein the biomarker of interest is lactate dehydrogenase.

4. The method of claim 1 wherein the bioluminescent emission is a directly produced reaction product.

5. The method of claim 1 wherein the bioluminescent emission is a reaction product enzymatically coupled to the formation of the reduced form of NAD or NADP.

6. A nonreferenced and automated method for quantifying at least one of a complex mixture of tissue-specific isoenzymes in an aqueous media comprising the steps of:
   (a) resolving the complex mixture into discernable isoenzyme components by liquid chromatography;
   (b) contacting a predetermined amount of the resolved components with at least one or more reactants in an amount effective to produce an ordered sequence of reactions wherein:
      (A) in a first reaction, at least one resolved component produces as a product the reduced form of NAD or NADP;
      (B) in a second reaction, said reduced form is oxidized in the presence of flavin oxidoreductase to produce the reduced form of riboflavin and NAD or NADP; and
      (C) in a third reaction, the reduced form of riboflavin is oxidized in the presence of oxygen, dodecanal, and bacterial luciferase to produce a bioluminescent emission accurately confirming the presence of the at least one resolved component;
   and
   (c) correlating said emission to the concentration of the at least one resolved component.

* * * * *